United States Patent
Koken et al.

(10) Patent No.: US 11,540,800 B2
(45) Date of Patent: Jan. 3, 2023

(54) DETERMINATION OF A SUBJECT PROFILE WITH A CAMERA

(71) Applicant: KONINKLIJKE PHILIPS N.V., Eindhoven (NL)

(72) Inventors: Peter Koken, Hamburg (DE); Julien Senegas, Hamburg (DE); Martin Bergtholdt, Hamburg (DE)

(73) Assignee: Koninklijke Philips N.V., Einhoven (NL)

( * ) Notice: Subject to any disclaimer, the term of this patent is extended or adjusted under 35 U.S.C. 154(b) by 182 days.

(21) Appl. No.: 16/756,135

(22) PCT Filed: Oct. 12, 2018

(86) PCT No.: PCT/EP2018/077812
§ 371 (c)(1),
(2) Date: Apr. 15, 2020

(87) PCT Pub. No.: WO2019/076734
PCT Pub. Date: Apr. 25, 2019

(65) Prior Publication Data
US 2020/0237334 A1    Jul. 30, 2020

(30) Foreign Application Priority Data

Oct. 16, 2017    (EP) .................................... 17196513

(51) Int. Cl.
*A61B 5/05*    (2021.01)
*A61B 6/00*    (2006.01)
(Continued)

(52) U.S. Cl.
CPC ............ *A61B 6/545* (2013.01); *A61B 5/0077* (2013.01); *A61B 5/055* (2013.01); *A61B 5/1079* (2013.01);
(Continued)

(58) Field of Classification Search
CPC ....... A61B 5/055; A61B 5/0077; A61B 6/037; A61B 6/545; A61B 6/0407
See application file for complete search history.

(56) References Cited

U.S. PATENT DOCUMENTS 6,421,551 B1    7/2002    Kuth et al.
2008/0108892 A1    5/2008    Ritter
(Continued)

FOREIGN PATENT DOCUMENTS

JP    2015181891 A    10/2015

OTHER PUBLICATIONS

Grimm R, "Markerless estimation of patient orientation, posture and pose using range and pressure imaging : for automatic patient setup and scanner initialization in tomographic imaging" International journal of computer assisted radiology and surgery (vol. 7, issue 6, pp. 921-929) Nov. 2012.

(Continued)

*Primary Examiner* — Joel F Brutus (57)    ABSTRACT

The invention provides for a medical apparatus (100, 300, 400) comprising a subject support (102) configured for moving a subject (106) from a first position (124) to a second position (130) along a linear path (134). The subject support comprises a support surface (108) for receiving the subject. The subject support is further configured for positioning the subject support in at least one intermediate position (128). The subject support is configured for measuring a displacement (132) along the linear path between the first position and the at least one intermediate position. Each of the at least one intermediate position is located between the first position and the second position. The medical apparatus further comprises a camera (110) configured for imaging the support surface in the first position. Execution of machine executable instructions 116 cause the a processor (116) controlling the medical apparatus to:

(Continued)

acquire (200) an initial image (142) with the camera when the subject support is in the first position; control (202) the subject support to move the subject support from the first position to the second position; acquire (204) at least one intermediate image (144) with the camera and the displacement for each of the at least one intermediate image as the subject support is moved from the first position to the second position; and calculate (206) a height profile (150, 600, 604) of the subject by comparing the initial image and the at least one intermediate image. The height profile is at least partially calculated using the displacement. The height profile is descriptive of the spatially dependent height of the subject above the support surface.

20 Claims, 7 Drawing Sheets (51) Int. Cl.
    *G06T 7/11* (2017.01)
    *G06T 7/70* (2017.01)
    *H04N 5/232* (2006.01)
    *A61B 5/00* (2006.01)
    *A61B 5/107* (2006.01)
    *A61B 6/03* (2006.01)
    *A61B 6/04* (2006.01)
    *A61N 5/10* (2006.01)
    *G06T 5/00* (2006.01)
    *G06T 7/00* (2017.01)
    *H04N 5/225* (2006.01)
    *H04N 7/18* (2006.01)
    *A61B 5/055* (2006.01)

(52) U.S. Cl.
    CPC .............. *A61B 6/032* (2013.01); *A61B 6/037* (2013.01); *A61B 6/0407* (2013.01); *A61B 6/4417* (2013.01); *A61N 5/1049* (2013.01); *G06T 5/002* (2013.01); *G06T 7/0014* (2013.01); *G06T 7/11* (2017.01); *G06T 7/70* (2017.01); *H04N 5/2253* (2013.01); *H04N 5/23299* (2018.08); *H04N 7/183* (2013.01); *A61N 2005/1052* (2013.01); *A61N 2005/1055* (2013.01); *A61N 2005/1059* (2013.01); *G06T 2207/30004* (2013.01); *G06T 2207/30196* (2013.01)

(56) References Cited

U.S. PATENT DOCUMENTS

| | | |
|---|---|---|
| 2011/0154569 A1 | 6/2011 | Wiggers et al. |
| 2011/0193953 A1* | 8/2011 | Sones ..................... H04N 7/18 348/135 |
| 2013/0342851 A1 | 12/2013 | Fresel et al. |
| 2015/0281680 A1 | 10/2015 | Grafenberg |
| 2016/0092078 A1 | 3/2016 | Braun et al. |
| 2016/0174930 A1 | 6/2016 | Braun et al. |
| 2017/0091939 A1 | 3/2017 | Kluckner et al. |
| 2017/0100089 A1 | 4/2017 | Chang et al. |
| 2017/0200317 A1 | 7/2017 | Hannemann et al. |
| 2017/0311842 A1* | 11/2017 | Boettger .............. A61B 6/0407 |

OTHER PUBLICATIONS

International Search Report from PCT/2018/077812 dated Jan. 31, 2019.

Watanabe et al. "An Improvement in Accuracy of the Small Electronic Devices Inspection by Means of a Single Camera Stereo Method" Vision Technology Practical Application Workshop, The Japan Society for Precision Engineering, Dec. 8, 2005 p. 105-110 (no translation available).

* cited by examiner

DETERMINATION OF A SUBJECT PROFILE WITH A CAMERA

CROSS REFERENCE TO RELATED APPLICATIONS

This application is a U.S. national phase application of International Application No. PCT/EP2018/077812 filed on Oct. 12, 2018, which claims the benefit of EP Application Serial No. 17196513.0 filed on Oct. 16, 2017 and is incorporated herein by reference.

FIELD OF THE INVENTION

The invention relates to three dimensional medical imaging modalities such as magnetic resonance imaging, positron emission tomography, single photon emission tomography, and computed tomography; in particular to the positioning of a subject for one of these modalities.

BACKGROUND OF THE INVENTION

In three dimensional imaging modalities such as magnetic resonance imaging, positron emission tomography, single photon emission tomography, and computed tomography a subject is brought into a position where the medical imaging system is able to acquire medical imaging data that is descriptive of a three dimensional volume of the subject within an imaging volume. To properly image a subject it is therefore important to be able to identify the portion of the subject that is desired to be imaged and bring this portion within the imaging volume.

United States patent application publication US 2013/0342851 A1 discloses a method for gathering information relating to at least one object positioned on a patient positioning device of a medical imaging device is provided. The method includes the following steps: gathering by optical means of 3-D image data relating to the object positioned on the patient positioning device by means of a 3-D image data recording unit; transferring the gathered 3-D image data from the 3-D image data recording unit to an evaluating unit; determining information relating to the object positioned on the patient positioning device based on the 3-D image data by means of the evaluating unit; generating output information based on the determined information relating to the object positioned on the patient positioning device; and outputting the output information relating to the object positioned on the patient positioning device.

SUMMARY OF THE INVENTION

The invention provides for a medical apparatus, a computer program product and a method in the independent claims. Embodiments are given in the dependent claims.

Embodiments of the invention may provide for a medical apparatus that comprises a subject support and a camera. The medical apparatus is configured to acquire multiple images of a subject that is reposing on the subject support for multiple positions of the subject support. For these multiple positions, there is a known displacement between them. By examining the multiple images a height profile of the subject can be calculated. A height profile as used herein is spatially dependent mapping of the height of the subject above the subject support. Embodiments may enable the use of a two dimensional camera to be used to determine the height profile. In other embodiments, a three dimensional camera may be used. The acquisition of multiple three dimensional images with the three dimensional camera may enable the determination of a more accurate height profile.

In one aspect of the invention, the subject support and the camera are moveable relative to one another in that at least one of the subject support and the camera, or both, are movable along a linear path. The subject support and the camera are moveable between a first and a second position relative to one another. The subject support and the camera are configured for measuring a displacement relative to each other along a linear path between the first position and at least one intermediate position. Each of the at least one intermediate position is located between the first position and the second position. At the first position of the subject support and the camera relative to each other an initial image is acquired by the camera and at one or a series of intermediate relative positions of the subject support and the camera one or more intermediate images are acquired.

Execution of the machine-executable instructions further cause the processor to calculate a height profile of the subject by comparing the initial image and the at least one intermediate image. The height profile is at least partially calculated using the displacement of the subject support and the camera relative to each other. The height profile is descriptive of the spatially dependent height of the subject above the support surface. This embodiment may be beneficial because it may provide for an improved means of measuring a height profile of the subject using a single camera.

The invention also relates to a computer programme comprising instructions to derive the height profiles from images acquired at different relative positions of the camera and the subject support.

The invention also relates to a method to operate the medical apparatus to derive the height profiles from images acquired at different relative positions of the camera and the subject support.

In one aspect, the invention provides for a medical apparatus comprising a subject support configured for moving a subject from a first position to a second position along the linear path. The subject support further comprises a support surface for receiving the subject. The subject support is further configured for positioning the subject support in at least one intermediate position. The subject support is configured for measuring a displacement along a linear path between the first position and at least one intermediate position. Each of the at least one intermediate position is located between the first position and the second position.

The medical apparatus further comprises a camera configured for imaging the support surface in the first position. The camera is also configured for imaging a subject reposing on the support surface. The medical apparatus further comprises a memory containing machine-executable instructions. The medical apparatus further comprises a processor for controlling the medical apparatus.

Execution of the machine-executable instructions further cause the processor to acquire an initial image with the camera when the subject support is in the first position. An initial image as used herein is an image. The "initial" in initial image is a label to identify a particular image.

Execution of the machine-executable instructions further cause the processor to control the subject support to move the subject support from the first position to the second position. Execution of the machine-executable instructions further cause the processor to acquire the at least one intermediate image with the camera and the displacement of the subject support for each of the at least one intermediate image as the subject support is moved from the first position to the second position. Each of the at least one intermediate image is an image. The "intermediate" in intermediate image is a label to identify a particular image.

There may be a number of intermediate images and each intermediate image that is acquired is associated with or referenced by the position or displacement that the subject support has undergone.

Execution of the machine-executable instructions further cause the processor to calculate a height profile of the subject by comparing the initial image and the at least one intermediate image. The height profile is at least partially calculated using the displacement of the subject support. The height profile is descriptive of the spatially dependent height of the subject above the support surface. This embodiment may be beneficial because it may provide for an improved means of measuring a height profile of the subject using a single camera.

The height profile may alternatively described as a distance profile between the subject and the camera. For example, in 3D imaging the natively acquired 3D data are range/depth data descriptive of the distance (along the optical axis) between the camera and the object. These can be converted into height profile above a given surface, if the coordinates of this surface in the camera coordinate system are known. Or by simply taking the difference between two images.

A height profile as used herein may either be a one-dimensional profile of the subject or it may be a two-dimensional image or mapping of the subject that describes the distance of the subject in terms of distance or displacement.

The medical apparatus may also have a calibration within the memory in some examples. For example, a graph paper or other object which has a discernible pattern may be placed on the support surface to perform a calibration. The support may then be moved from the first position to one or more of the intermediate positions and images acquired. This can be used to make a mapping of how the surface moves from the initial image to the intermediate images as a function of the subject support. If there is a subject or other object on top of the support surface, then those portions of the object or subject are closer to the camera than the support surface will be. This may have the effect of moving a larger distance between images than for something which is directly on the support surface and doesn't have a height.

As an alternative to having a calibration in the memory, the extrinsic parameters of the camera with respect to the medical apparatus are known, i.e. the 3×3 rotation matrix and 1×3 translation vector describing the angulations and position of the camera with respect to the reference coordinate system of the medical apparatus.

This may allow to transform the coordinates of a pixel in the camera image into 3D coordinates of the corresponding point in the coordinate system of the medical apparatus.

As a further alternative, if the camera is not calibrated with respect to the medical apparatus, a height profile of the subject can still be derived by processing the camera images alone, however in this case the absolute position would not be known.

In another embodiment, the camera is a two-dimensional camera. The height profile is calculated by detecting pixel displacements between combinations of the initial image and the at least one intermediate image. The pixel displacements may be considered to be analogous to a parallax effect. The combination may be specifically between the initial image and each of the at least one intermediate image.

This embodiment may be beneficial because it enables the making of the height profile without a three-dimensional camera.

The camera used for the two-dimensional camera may take different forms in different examples. For example it may be a color, a monochrome, a visible, an infrared, or a thermal camera.

In another embodiment, the pixel displacements are used to calculate the height profile by dividing the initial image and the at least one intermediate image into multiple pixel regions. Using the pixel displacements may further comprise identifying the displacement of each of the pixel regions. Using the pixel displacements may further comprise calculating the height profile by comparing the displacement of each of the multiple pixel regions to the displacement of the subject support. The displacement of the subject support within the images may for example be known ahead of time from a calibration or may be known in advance 2017PF02331 from the measurement of the subject support position. The dividing of the initial image and the at least one intermediate image into different pixel regions may be in some examples performed using known video processing and codex algorithms. For example in video compression it is common that regions of the image which remain unchanged may be translated to reduce the amount of memory used by a video. In another example, the computing of the disparity between images using cross-correlation in stereovision may also be used. Such known algorithms may be used to identify regions of the initial image and the at least one intermediate image and calculate a mapping for groups of these pixel regions which can then be used to calculate the height above the support surface.

In another embodiment, detecting pixel displacements between combinations of the initial image and the at least one intermediate image is used to perform any one of the following: reduce signal-to-noise by averaging multiple height calculations, reduce occluded regions using multiple height calculations of different combinations of the initial image and the at least one intermediate image, to identify and reduce regions with no height calculation by comparing multiple height calculations, and combinations thereof. For example, if more than one measurement of the height is made these multiple measurements can be used to perform averaging or other statistical measures to reduce the signal noise. Likewise, when the camera is aimed at a subject there may be portions of the subject which are not visible for all positions of the subject support. As the subject support is moved different regions of the subject may become visible at different times. By calculating different combinations it may be possible to identify regions which are occluded during some positions and then to correct the profile. In some cases, because of lighting or the way the image appears in the 2D image, some regions may not be able to have their height identified or calculated. If a larger number of intermediate positions have images acquired then this may enable the larger amount of data to be used to fill in such regions where there are no height calculations.

In another embodiment, the camera is a three-dimensional camera. The initial image is an initial range image. The initial range image is a range image, and the "initial" in initial range image is a label to identify a specific range image. Each of the at least one intermediate images is also an intermediate range image. Each intermediate range image is a range image, and the "intermediate" in intermediate rage image is a label to indicate a specific range image.

The height profile is a combination of the initial image and the at least one intermediate image. In this embodiment a three-dimensional camera is used, and the different images for different subject support positions are used to improve the quality of the three-dimensional or range image. The term depth image or range image is considered to be synonymous in this application.

In another embodiment, the initial image and the at least one intermediate image are combined at least partially by averaging. For example the three-dimensional camera may make measurements of different positions of the subject support. These data from different positions can be combined and averaged to improve the accuracy of the combined image.

The distance from the camera to the support surface for different positions of the subject support can be measured ahead of time. This may be useful for calibrating the three-dimensional camera for performing embodiments of the invention. This may also enable the camera to be mounted at oblique angles with respect to the linear path of the subject support.

In another embodiment, the initial image and the at least one intermediate image are combined such that the occluded regions from the height profile are removed. For example in different positions of the subject support not all surfaces of the subject may be visible to the camera. By taking multiple images at different subject support positions these occluded regions from particular images can be removed by combining the measurements.

In another embodiment, the medical apparatus further comprises a medical imaging system for acquiring medical image data from an imagine volume. Medical image data as used herein encompasses data that is acquired using a medical imaging system that is descriptive of a subject. The imaging volume as used herein encompasses a region or volume of space from which the medical imaging system is able to acquire the medical image data. The subject support is configured for moving the subject support into an imaging position, wherein in the imaging position at least a portion of the subject support is within the imaging volume. In this embodiment the subject support enables a subject to be moved or at least partially moved into an imaging volume of the medical imaging system.

In another embodiment, the camera is mounted on a ceiling above the subject support. This for example may be beneficial because it may enable the camera to be mounted such that it acquires images which are in the same plane as the displacement along the linear path. This may make the mathematical calculation of the height profile more straight forward.

In another embodiment, the camera has an optical axis. The optical axis is perpendicular to the linear path.

In another embodiment, the camera is mounted on the medical imaging system. This may have the benefit that the mounting of the camera on the medical imaging system reduces the amount of work or preparation for installing the medical imaging system. For example if the camera is mounted on the medical imaging system itself the camera can be preinstalled and then shifted along with the medical imaging system. If the camera is installed on a separate platform or on a ceiling then wiring and other preparations and mounting need to be performed on the site.

In another embodiment, execution of the machine-executable instructions further cause the processor to fit a subject model to the height profile. The subject model may for example be a three-dimensional or surface model which can be deformed or fit to the height profile. There may also be various registrations which are attached or associated to the subject model. Fitting a subject model to the height profile may therefore enable the identification of regions which may be desired to be imaged.

In another embodiment, execution of the machine-executable instructions further cause the processor to determine a region of interest using the subject model. For example a particular imaging protocol may be interested in imaging a specific body part or region. Fitting the subject model to the height profile may enable automatic identification of this region.

In another embodiment, execution of the machine executable instructions cause the processor to determine a region of interest by performing landmark detection on the height profile. The three dimensional structure of the height profile may be used to identify portions or regions of the subject.

In another embodiment, execution of the machine-executable instructions further cause the processor to control the subject support to move the region of interest within the imaging volume.

In another embodiment, execution of the machine-executable instructions further cause the processor to control the medical imaging system to acquire the medical image data and then to reconstruct a medical image from the medical image data.

In another embodiment, execution of the machine-executable instructions further cause the processor to perform any one of the following: use the subject model and/or the height profile to perform a collision prediction with the medical imaging system, calculate an SAR or specific absorption estimate using the subject model and/or the height profile when performing magnetic resonance imaging, calculate a subject weight using the subject model and/or the height profile, calculate a subject height using the subject model and/or the height profile, and combinations thereof. Any of the above may be beneficial because it may expedite or help in the preparation of a medical imaging protocol.

In another embodiment, the medical imaging system is a magnetic resonance imaging system.

In another embodiment, the medical imaging system is a positron emission tomography system.

In another embodiment, the medical imaging system is a single photon emission tomography system.

In another embodiment, the medical imaging system is a computed tomography system or CT system.

In another embodiment, the medical imaging system is a combined positron emission tomography and magnetic resonance imaging system.

In another embodiment, the medical imaging system is a combined computed tomography and radiation therapy system.

In another embodiment, the medical imaging system is a combined computed tomography and positron emission tomography system.

In another embodiment, the medical imaging system is a combined magnetic resonance imaging system and radiation therapy system.

In another embodiment, the initial image and the at least one intermediate image are acquired as a video feed. For example, the camera may repeatedly acquire images without the subject support even stopping. The images in the video feed can be referenced or indexed to the displacement of the subject support. The individual images from the video feed may then be used to calculate the height profile. In some instances the use of the video feed may also help in the calculation of the height profile. This identification of various regions of pixels may for example be reused during the calculation of the height profile.

In another aspect, the invention provides for a computer program product comprising machine-executable instructions for execution by a processor controlling the medical apparatus. The medical apparatus comprises a subject support configured for moving a subject from a first position to a second position along a linear path. The subject support comprises a support surface for receiving the subject. The subject support is further configured for positioning the subject support in at least one intermediate position. The subject support is configured for measuring a displacement along the linear path between the first position and the at least one intermediate position. Each of the at least one intermediate position is located between the first position and the second position. The medical apparatus further comprises a camera configured for imaging the support surface in the first position.

Execution of the machine-executable instructions cause the processor to acquire an initial image with the camera when the subject support is in the first position. Execution of the machine-executable instructions further cause the processor to control the subject support to move the subject support from the first position to the second position. Execution of the machine-executable instructions further cause the processor to acquire at least one intermediate image with the camera and the displacement of the subject support for each of the at least one intermediate image as the subject support is moved from the first position to the second position. Execution of the machine-executable instructions further cause the processor to calculate a height profile of the subject by comparing the initial image and the at least one intermediate image. The height profile is at least partially calculated using the displacement. The height profile is descriptive of the spatially dependent height of the subject above the subject support.

In another aspect, the invention provides for a method of operating a medical apparatus. The medical apparatus comprises a subject support configured for moving a subject from a first position to a second position along a linear path. The subject support comprises a support surface for receiving the subject. The subject support is further configured for positioning the subject support in at least one intermediate position. The subject support is configured for measuring a displacement along the linear path between the first position and the at least one intermediate position. Each of the at least one intermediate positions is located between the first position and the second position. The medical apparatus further comprises a camera configured for imaging the support surface in the first position. The camera may also be configured to at least partially image the support surface when the subject support is in the at least one intermediate position.

The method comprises acquiring an initial image with the camera when the subject support is in the first position. The method further comprises controlling the subject support to move the subject support from the first position to the second position. The method further comprises acquiring at least one intermediate image with the camera and the displacement for each of the at least one intermediate image as the subject support is moved from the first position to the second position. The method further comprises calculating a height profile of the subject by comparing the initial image and the at least one intermediate image. The height profile is at least partially calculated using the displacement. The height profile is descriptive of the spatially dependent height of the subject above the subject support.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

A medical imaging system as used herein is a medical device configured for acquiring medical image data from an imaging volume. Medical image data is data which is descriptive of a volume of a subject within the imaging volume. Medical image data may be reconstructed into or rendered as one or more medical images.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical image data. A Magnetic Resonance (MR) image or magnetic resonance image data is defined herein as being the reconstructed two or three dimensional visualization of anatomic data contained within the magnetic resonance data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
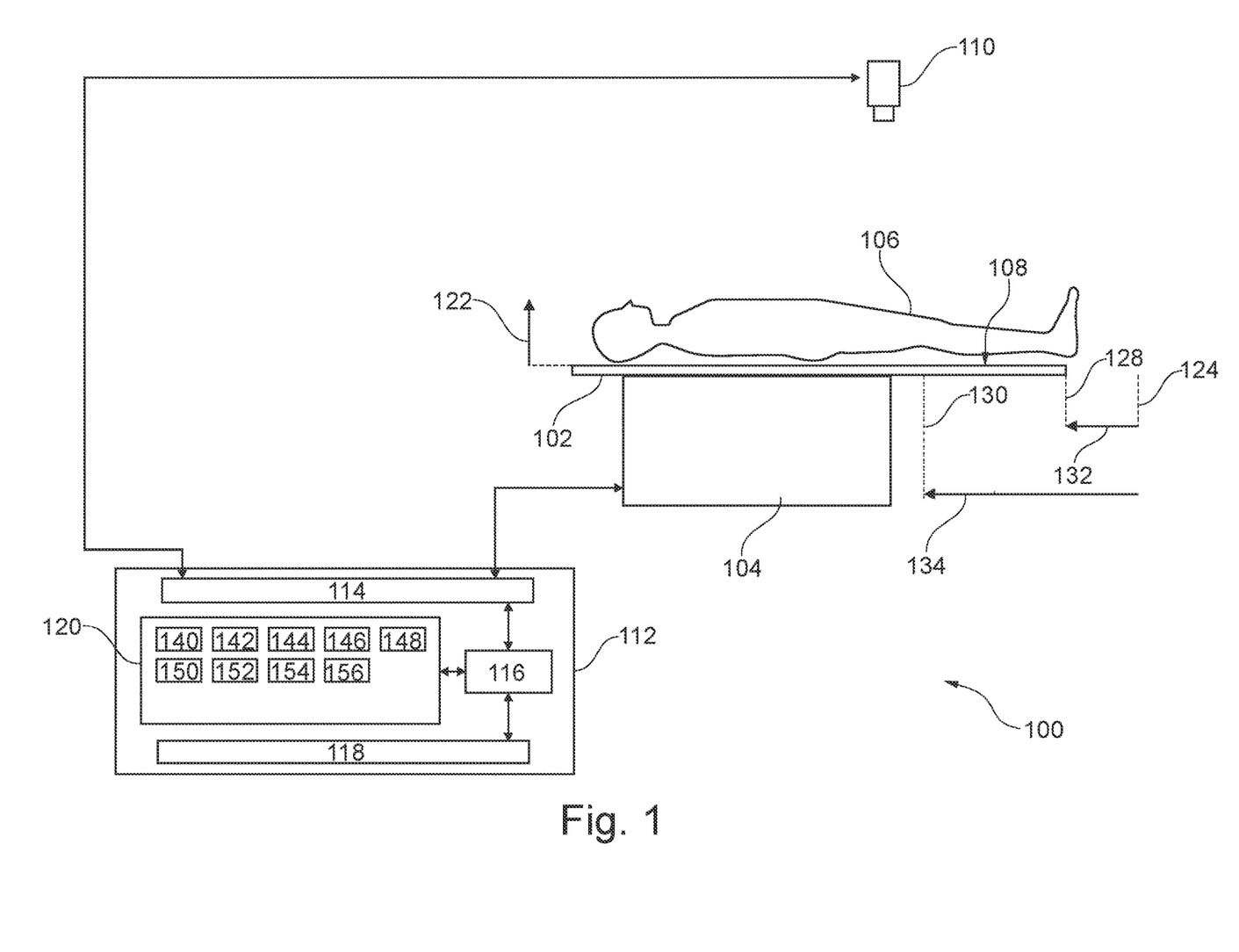
FIG. 1 illustrates an example of a medical apparatus.

FIG. 1 illustrates an example of a medical apparatus 100. The medical apparatus is shown as comprising a subject support 102. The subject support 102 comprises an actuator 104 which is constructed to move the subject support 102 a controlled distance or displacement along a linear path 134. There is a subject 106 reposing on a support surface 108. The support surface 108 is facing a camera 110. The camera 110 is able to acquire images of the support surface 108 and/or the subject 106 when the subject support 102 is in various positions. The medical apparatus 100 is further shown as comprising a computer 112. The computer 112 comprises a hardware interface 114 that enables a processor 116 to communicate with and control the other components of the medical apparatus 100.

Specifically in this FIG. the hardware interface 114 is shown as interfacing with the camera 110 to acquire images and with the actuator 104 to control the position of the subject support 102. In other examples or embodiments the hardware interface 114 may be used to control additional components.

The processor 116 is in communication with the hardware system 142, a memory 120, and a user interface 118. The memory 120 may be any combination of memory which is accessible to the processor 1116. This may include such things as main memory, cached memory, and also non-volatile memory such as flash RAM, hard drives, or other storage devices. In some examples the memory 1120 may be considered to be a non-transitory computer-readable medium.

The arrow 122 indicates a height or distance above the support surface 108. The dashed line 124 indicates the location of an edge of the subject support 102 when the subject support is in the first position 124. The dashed line 130 indicates the position of the edge of the subject support 102 when the subject support 102 is in the second position 130. The dashed line 128 shows the current position of the edge of the subject support 102. The subject support 102 is currently in an intermediate position 128. As the subject support 102 is moved to different displacements 132, 134 with respect to the first position 124, images are acquired with the camera 110. Portions of the subject 106 that are closer to the camera 110 than the support surface 108 may move larger within the multiple images than the support surface 108.

For example, a graph or other pattern could be placed on the support surface 108 and the support surface could be imaged in multiple positions. This may provide information on how the displacements 132, 134 relate to pixel displacement of images of the support surface 108. When a subject 106 is placed on the support surface 108 the pixels which represent identical portions of the subject 106 will move a larger amount than what would move if the support surface 108 alone were moved. This larger movement of individual pixels or groups of pixels may be used to develop a 3D measurement of the distance of the surface of the subject 106 above 122 the support surface 108.

The memory 120 is shown as containing machine-executable instructions 140. The machine-executable instructions 140 enable the processor 116 to control the operation and function of the medical apparatus 100. The memory 120 is further shown as containing an initial image 142 that was acquired when the subject support 102 was in the first position 124. The memory 120 further shows an intermediate image 144 being stored. The intermediate image was acquired when the subject support 102 was in the intermediate position 128. The subject support 102 in FIG. 1 is depicted as being in the intermediate position 128. The memory 120 is further shown as containing a displacement 146. The displacement 146 may for example be a numerical value which indicates a distance indicated by the vector 132.

The memory 120 is further shown as containing an optional calibration 148. The calibration 148 may for example be used to simplify the calculation of a height profile 150. The height profile 150 is shown as being stored in the memory 120 also. The height profile 150 may be calculated using the initial image 142, the intermediate image 144, and a knowledge of the displacement 146. If additional intermediate images 144 are constructed the various combinations of displacements between various combinations of images may be used to further refine and improve the determination of the height profile 150. The memory 120 is further shown as containing a subject model 152. The subject model 152 may for example be a volume or surface model which is deformed or fit to the height profile 150. The subject model 152 may be for example able to derive useful information such as a registration 154 for a region of interest or may be used to derive data 156 descriptive of the subject, such things as an estimate of the subject size, height, and/or weight.

Figure 2:
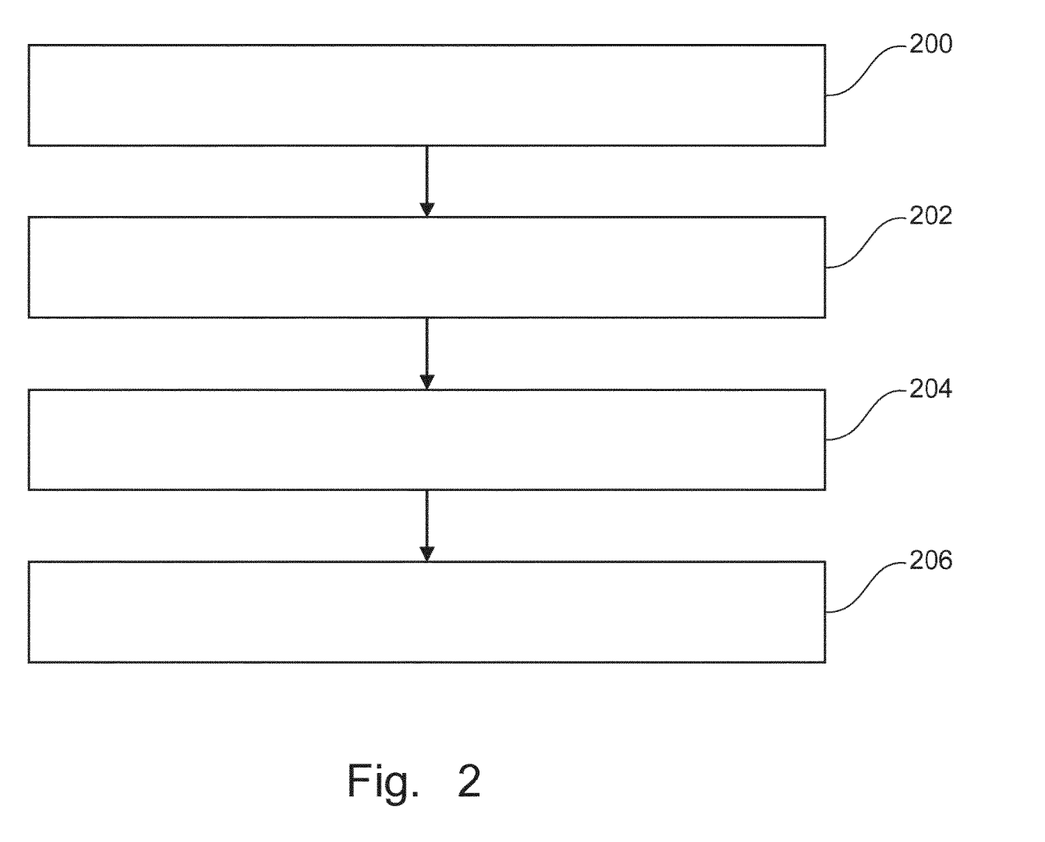
FIG. 2 shows a flow chart which illustrates an example of a method of operating the medical apparatus of FIG. 1.

FIG. 2 shows a flowchart which illustrates a method of operating the medical apparatus 100 of FIG. 1. First in step 200, when the subject support 102 is in the first position 124 the camera 110 acquires the initial image 142. Next in step 202, the subject support 102 is moved from the first position 124 to the second position 130. As the subject support 102 is being moved from the first position 124 to the second position 130 step 204 is performed. In step 204 at least one intermediate image 144 is acquired with the camera 110 and the displacement 132 is also recorded. Finally, in step 206 a height profile 150 is calculated by comparing the initial image 142, the intermediate image 144, and using the displacement 146.

Figure 3:
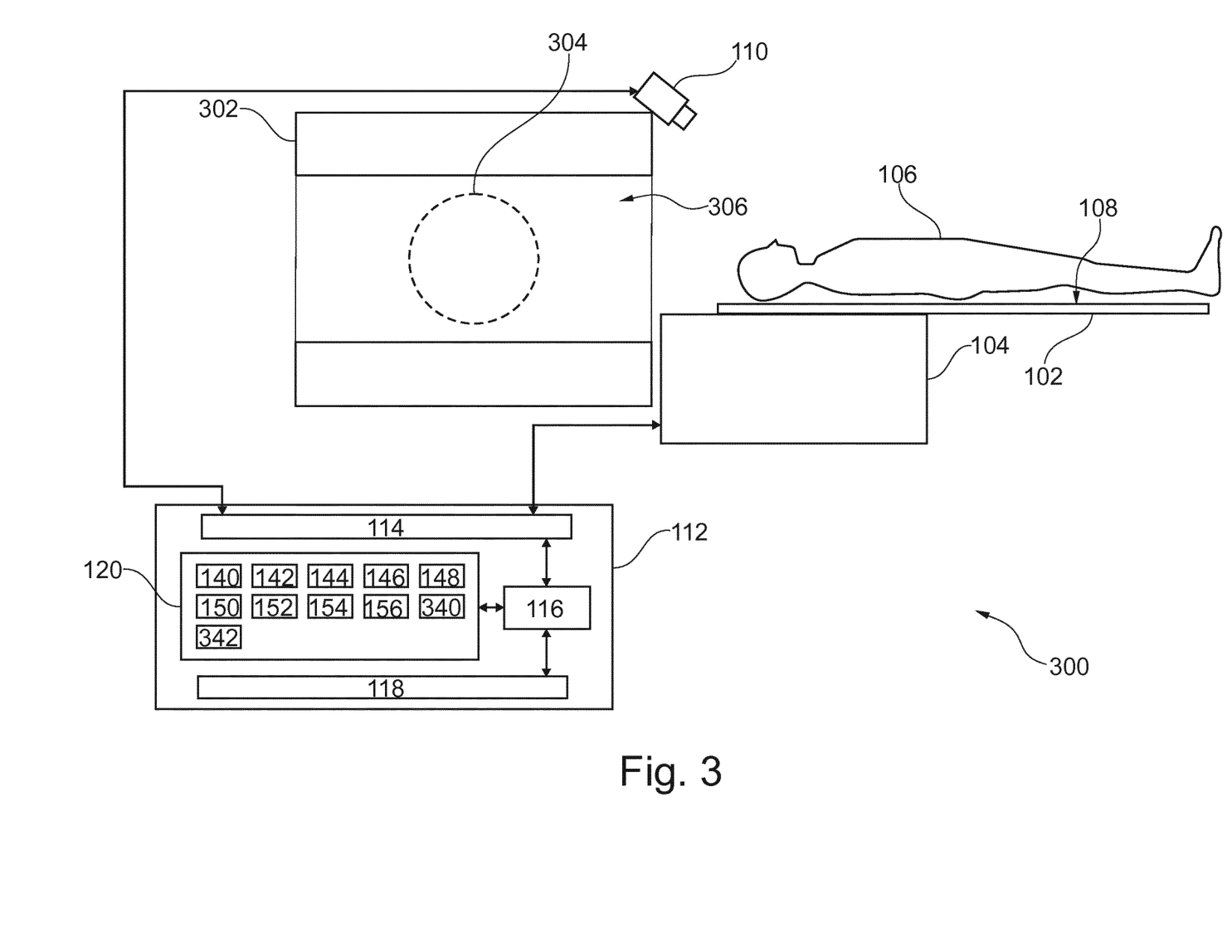
FIG. 3 illustrates a further example of a medical apparatus.

FIG. 3 illustrates a further example of a medical apparatus 300. The medical apparatus in FIG. 300 is similar to the medical apparatus 100 in FIG. 1 except there is now additionally a medical imaging system 302. The medical imaging system has a medical imaging volume 304 from which medical imaging data can be acquired. The subject support 102 is configured for moving at least a portion of the subject 106 into the medical imaging volume 304. In this example the medical imaging system 302 is cylindrical and has a bore 306 which the subject 106 can be moved into using the subject support 102. This is however not necessary, not all medical imaging systems 302 need to be cylindrically symmetric as is illustrated in this FIG. Additionally, it should be noted that the camera 110 is now mounted onto the medical imaging system 302 and aimed at an oblique angle to the support surface 108. This may make the mathematical calculation of the height profile 150 more difficult but it has the advantage that there are no additional mounting requirements for placing the camera 110 for example on a ceiling. The memory 120 is further shown as containing medical image data 340 that has been acquired when the subject 106 was at least partially within the imaging volume 304. The memory 120 is also further shown as containing a medical image that has been reconstructed from the medical image data 340.

Figure 4:
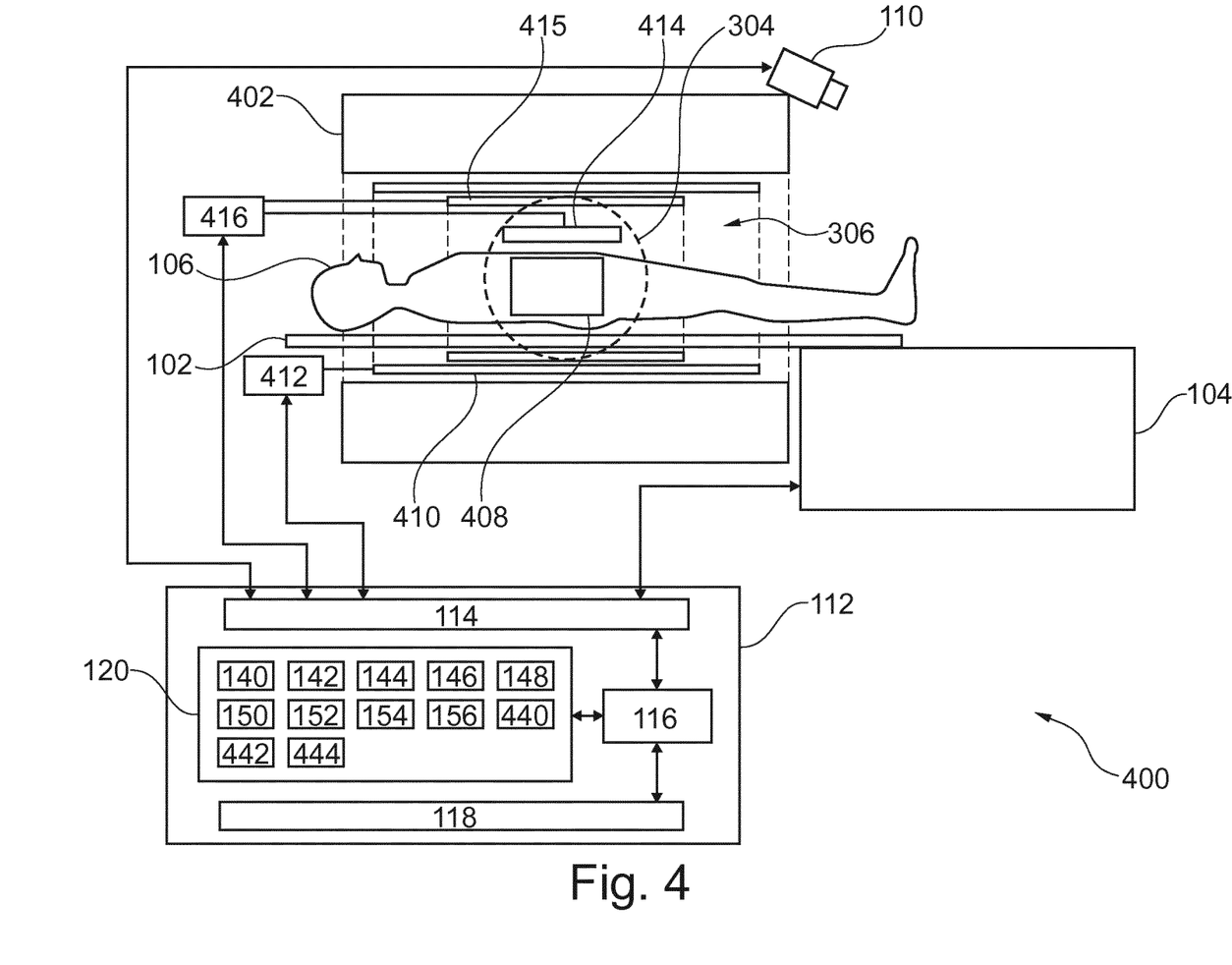
FIG. 4 illustrates a further example of a medical apparatus.

FIG. 4 shows a further example of a medical apparatus 400. The medical apparatus 400 in FIG. 4 is similar to the medical apparatus 300 in FIG. 3. However, in this example, the medical imaging system is a magnetic resonance imaging system 402. The magnetic resonance imaging system 402 comprises a main magnet 404, which may be referred to as the magnet. The magnet 404 is a superconducting cylindrical type magnet 404 with a bore 306 through it. The use of different types of magnets is also possible. Inside the cryostat of the cylindrical magnet, there is a collection of superconducting coils. Within the bore 306 of the cylindrical magnet 404 there is an imaging volume 304 where the magnetic field is strong and uniform enough to perform magnetic resonance imaging.

Within the bore 406 of the magnet there is also a set of magnetic field gradient coils 410 which is used for acquisition of magnetic resonance data to spatially encode magnetic spins within the imaging volume 304 of the magnet 404. The magnetic field gradient coils 410 are connected to a magnetic field gradient coil power supply 412. The magnetic field gradient coils 410 are intended to be representative. Typically, magnetic field gradient coils 410 contain three separate sets of coils for spatially encoding in three orthogonal spatial directions. A magnetic field gradient power supply supplies current to the magnetic field gradient coils. The current supplied to the magnetic field gradient coils 410 is controlled as a function of time and may be ramped or pulsed.

Adjacent to the imaging volume 304 in a magnetic resonance coil or antenna 414 that functions as radio-frequency antennas for manipulating the orientation of magnetic spins within the imaging volume 304 and for receiving radio transmissions from spins also within the imaging volume 304. The radio frequency coil may also be multiple coil elements. The radio frequency antenna may also be referred to as channel. The coil 414 is connected to a radio frequency transceiver 416. The coil 414 and radio frequency transceiver 316 may have separate transmitters and receivers. The coil 414 and the transceiver 116 form a radio-frequency system.

The coil 414 may be made of multiple coil elements, which may be used to acquire magnetic resonance data separately. The coil elements may therefore be used for a parallel imaging magnetic resonance technique. An optional body coil 415 is also shown. The body coil 415 would be useful in the parallel imaging technique as it could take acquired data at the same time as the individual coil elements and be used for calculating a set of coil sensitivities. The magnetic resonance data may be acquired from within the imaging volume 304. The magnetic resonance data is an example of medical image data.

Within the bore 306 of the magnet 404 the subject support 102 is shown as supporting a portion of the subject 106 in the imaging volume 304.

The transceiver 116, the actuator of the subject support 104, and the camera 110 are shown as being connected to the hardware interface 114 of the computer system 112. Within the memory 120 are located machine-executable instructions 140. The machine-executable instructions 140 enable the processor to control the operation and function of the medical apparatus 400 including the magnetic resonance imaging system 402 via the hardware interface 114.

The computer memory 120 is further shown as containing pulse sequence commands 440. The pulse sequence commands 440 are either instructions or data which can be transformed into instructions which may be used to control the magnetic resonance imaging system 402 to acquire magnetic resonance imaging data 442. The magnetic resonance imaging data 442 was acquired by controlling the magnetic resonance imaging system 402 with the pulse sequence commands 440. The machine-executable instructions may also enable the processor 116 to transform the magnetic resonance imaging data 442 into a magnetic resonance image 444. The magnetic resonance imaging data 442 is a specific example of medical image data 340. The magnetic resonance image 444 is a specific example of a medical image 342.

Within the imaging volume 304 there is a region of interest 408. The region of interest 408 may for example have been identified using the registration of the region of interest 154. The registration of the region of interest 154 may be used to control the position of the subject support 102 to place the region of interest 408 within the imaging volume 304.

Figure 5:
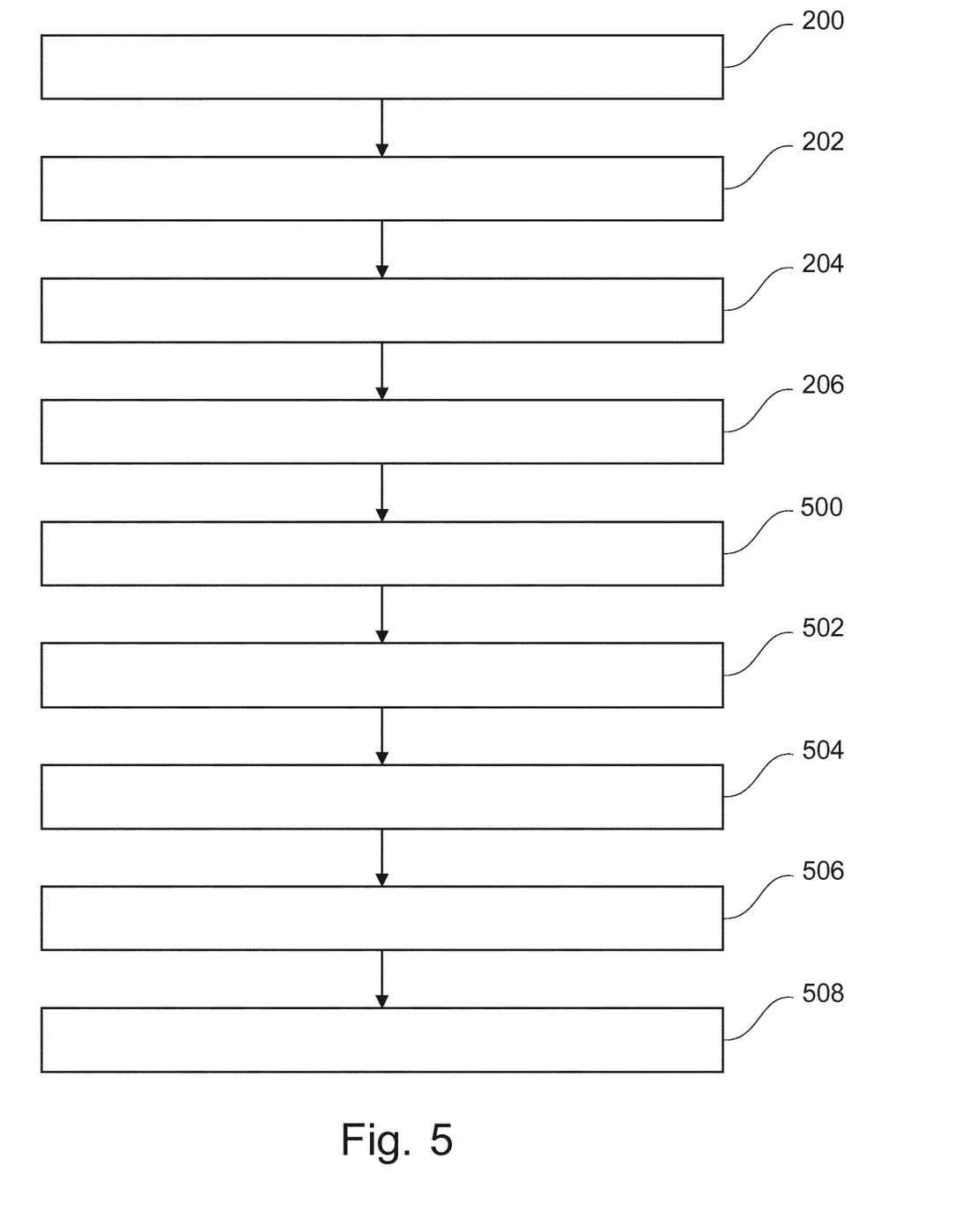
FIG. 5 shows a flow chart which illustrates an example of a method of operating the medical apparatus of FIG. 4.

FIG. 5 shows a flowchart which illustrates a method of operating the medical apparatus 400 of FIG. 4. The method in FIG. 5 is similar to the method in FIG. 2. Steps 200-206 are performed as they are performed in the method of FIG. 2. After step 206 the method proceeds to step 500. In step 500 a subject model 152 is fit to the height profile 150. The subject model 152 may for example be a deformable shape model. Next in step 502 a region of interest is determined using the subject model 152. For example, the subject model may provide the registration 154 of a particular region of interest. Then, in step 504, the processor 116 controls the actuator 106 to move the subject support such that the region of interest 408 is within the imaging volume 304. Next in step 506, the pulse sequence commands 440 are used to acquire the magnetic resonance imaging data 442. Finally in step 508, the magnetic resonance imaging data 442 is reconstructed into the magnetic resonance image 444.

A simple two dimensional (2D) camera, such as a 2D RGB camera, may be placed above the patient table in front of an MR system in combination with the acquisition of several 2D color images taken at different table positions. Using a depth from stereo algorithm, it is possible to generate depth information, without the need of a three dimensional (3D) camera. The 2D color images with depth information can be used for several workflow improvements.

Figure 6:
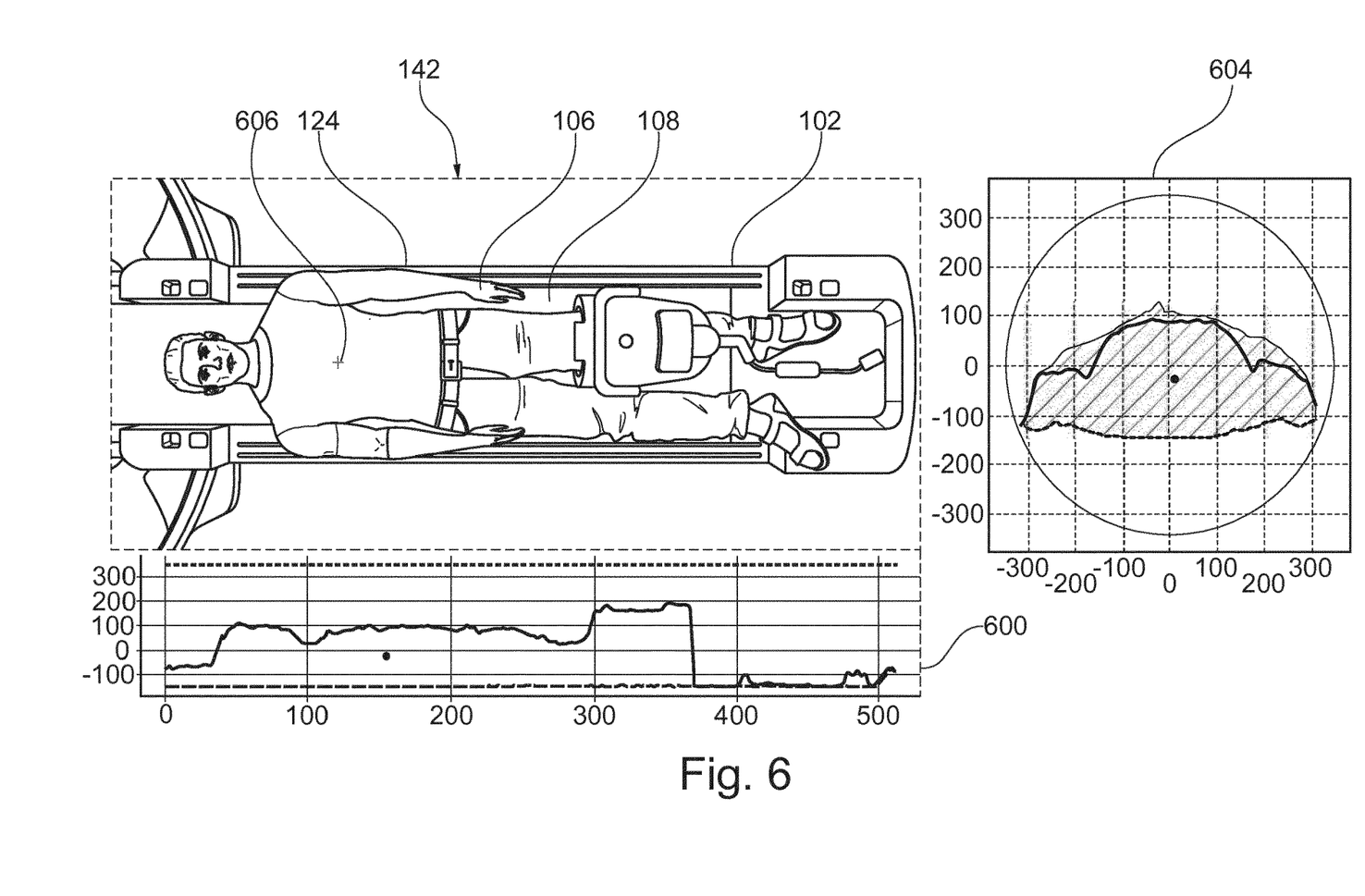
FIG. 6 shows an example of an image of a subject on a subject support acquired with a camera.

A 3D camera may be placed above the patient table in front of the magnet bore. The 2D color image in combination with the depth information can be used for several workflow improvements. It would be possible to replace the laser light visor and plan the reference position by clicking on the acquired image. In combination with the depth information provided by the 3D sensor, this allows to determine accurately the position of a target anatomy location in all three directions FIG. 6 shows an example of an initial image 142. In this case the initial image 142 was acquired using a color 2D camera. Several images were used to construct a height profile or three-dimensional image. 600 shows a sagittal cross-section of the height profile made from the image 142. The sagittal profile 600 passes through point 606 indicated on the image 142. 604 shows a transverse cross-section of the height profile calculated partially from image 142. The point 606 indicates a point where the transverse cross-section 604 passes through.

Other applications based on the combination of color and depth images may also be developed. The orientation and laterality of the patient could be determined automatically by image processing. Already mounted surface coils can be detected and the reference point can be set to their centre automatically. The SAR limits can be adapted by incorporating the actual body dimensions of the patient in the SAR model calculations. Automated collision detection for large patients can be introduced based on the 3D information. It would be possible to show different information as overlay to the color image: Size of the planned field of view (FOV), best coil position, size of the homogenous volume, etc.

A 3D camera is more expensive than regular 2D video camera and/or might not be available without license fees for the underlying technology. At least a second sensor, such as a time-of-flight sensor, is necessary to add depth information to a simple 2D color image. Spatial resolution of the depth sensors is generally much lower (typically below 640×480 pixels) than that of the color sensor. Due to the need of light-emitting source, these sensors are also associated with significant heating.

On the other hand, accurate geometrical information, as needed by all the applications above, can only be provided by a 3D optical system, and not with a simple 2D color image using any of the depth from stereo algorithms. The crucial difference to the standard setup of stereo imaging is, that here we do not have two cameras, but one camera takes two (or more) images with a fixed displacement relative to the object. Therefore only depth information on the moving parts can be computed (everything that is on the table). It should be noted, that uniformly colored regions are hard for stereo, since no clear correspondence can be established between individual pixels in both images. Several methods exist, however, to overcome this problem. First is to avoid uniform regions by using textured clothing and textures or special markers on top of the surface coils. If this is not possible, then methods employing regularization on spatial homogeneity can be employed.

Some examples may use a simple 2D camera such as a 2D RGB camera sensor placed above the patient table in front of the magnet, in combination with the acquisition of several 2D color images taken at different table positions. The camera could be positioned so as to image completely the patient lying on the table during exam preparation. After the initial image is acquired, the table is automatically moved a fix distance towards the magnet bore and immediately a second image is taken. Ideally, the patient did not move in-between and he is still completely visible on the second image. The two images can be used to generate the stereoscopic depth information of the patient. Several images at several table positions can be used to improve accuracy and reduce the number of occlusions.

Some embodiments may contain one or more of the following features:
1. Mount a camera, preferably in the scanner room, such that it images the whole space comprising patient table and patient when the table is outside of the scanner.
2. Calibrate the camera with respect to the MR system: determine the intrinsic parameters of the camera that allow mapping pixel coordinates in images taken by the camera and homogenous coordinates of the physical points in the camera coordinate system. Additionally, determine the extrinsic parameters of the camera that allow mapping into a reference coordinate system related to the MR scanner. The calibration may also be already stored in a memory of the system, in which case the calibration does not need to be performed every time.
3. Take an image during the patient preparation. Taking the suitable image can be either automatically triggered by analyzing a video stream from the camera to pick the right moment (i.e. when the patient lies on the table in the target final position but yet without additional devices such as coil attached), or performed manually as part of the selection process.
4. Take at least a second image at a different table position. This can be done by shifting the table by a fixed amount, either manually or automatically. Alternatively, this can be achieved by acquiring a series of images at consecutive table positions while moving the patient into the bore.
5. Compute the depth image by calculating for each pixel the pixel shift induced by the table displacement between the two images. This is known from stereoscopy and various algorithms have been proposed to solve this problem (cf. FIG. 7 below). Together with one of the 2D color images, the depth image can be presented to the operator for further planning Orientation, laterality, body size etc. can be calculated in the background.

Figure 7:
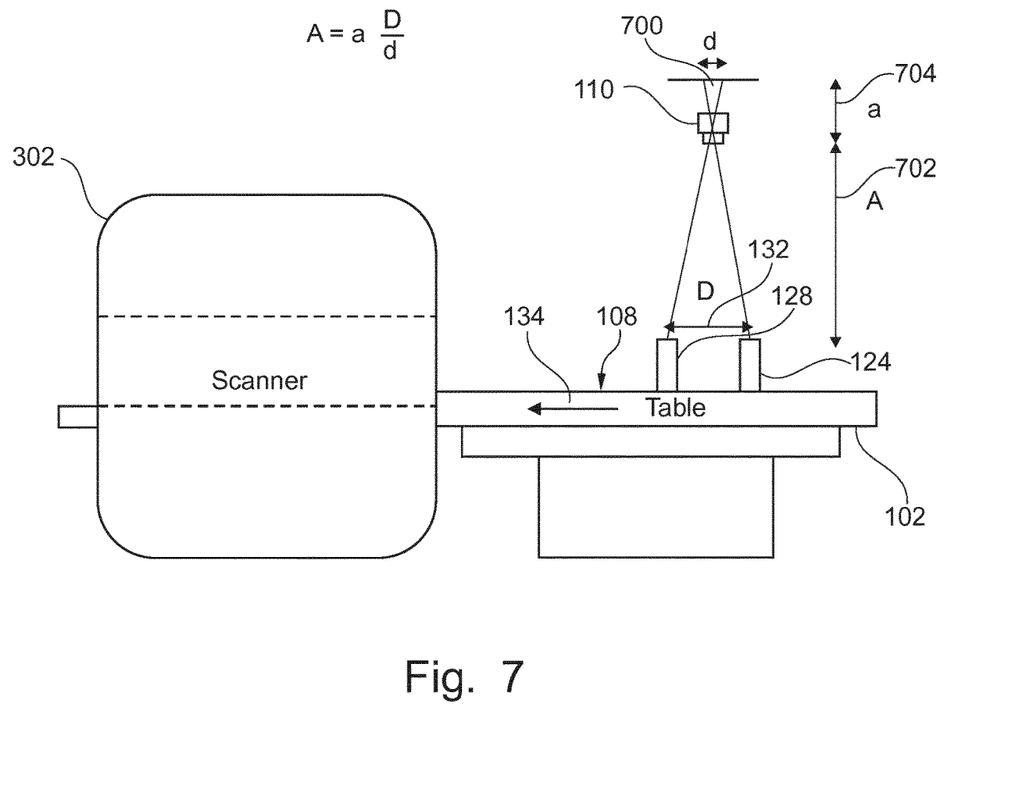
FIG. 7 illustrates a further example of a medical apparatus equivalent to the medical apparatus of FIG. 3.

FIG. 7 is used to illustrate how to calculate the height of an object above the support surface 108 following the assumption or model of a pinhole camera. The subject support 102 is moved such that the object goes from the initial position 124 to an intermediate position 128. This displacement of the subject support causes a displacement 132 of the object. The top portion of the object is a distance 702 from the optical origin of the camera 110 or the focal point of the camera 110 (in the pinhole model of a camera). Within the camera the focal distance is 704. This is the distance between the lens and the CCD. It can be seen from this FIG. that a distance in the height of the objects will result in a different displacement 700. This can be used to determine the height profile. In FIG. 7, The pixel shift d 700 induced by the known table displacement D 132 is proportional to the distance A 702 between the camera focal point and the object. The parameter a 704 is the distance between the camera image place and the focal point.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical apparatus
102 subject support
104 actuator
106 subject
108 support surface
110 camera
112 computer
114 hardware interface
116 processor
118 user interface
120 memory
122 height above support surface
124 position of subject support in first position
126 position of subject support in second position
128 position of subject support in intermediate position
130 displacement between subject support in first and second positions
132 displacement between subject support in first and intermediate position
134 linear path
140 machine executable instructions
142 initial image
144 intermediate image
146 displacement
148 calibration
150 height profile
152 subject model
154 registration of region of interest
156 data descriptive of subject
200 acquire an initial image with the camera when the subject support is in the first position
202 control the subject support to move the subject support from the first position to the second position
204 acquire at least one intermediate image with the camera and the displacement for each of the at least one intermediate image as the subject support is moved from the first position to the second position
206 calculate a height profile of the subject by comparing the initial image and the at least one intermediate image, wherein the height profile is at least partially calculated using the displacement
300 medical apparatus
302 medical imaging system
304 imaging volume
306 bore of medical imaging system
340 medical image data
342 medical image
400 medical apparatus
402 magnetic resonance system
404 main magnet
406 bore of magnet
408 region of interest
410 magnetic field gradient coils
412 gradient coil power supply
414 coil
415 body coil
416 transceiver
440 pulse sequence commands
442 magnetic resonance imaging data
444 magnetic resonance image
500 fit a subject model to the height profile
502 determine a region of interest using the subject model
504 control the subject support to move the region of interest within the imaging volume
506 acquire the magnetic resonance imaging data
508 reconstruct the magnetic resonance imaging data into the magnetic resonance image
600 sagittal cross section of height profile
604 transverse cross section of height profile
606 location in image
700 displacement in image
702 distance between camera lens and the object
704 distance between camera lens and the CCD

The invention claimed is:

1. A medical apparatus comprising:
a subject support for receiving a subject;
a camera configured for imaging a support surface of the subject support;
wherein the subject support and the camera are movable relative to one another along a linear path between a first position, at least one intermediate position and a second position, wherein the at least one intermediate position is located between the first position and the second position; a memory storing instructions;
a processor for controlling the medical apparatus, wherein execution of the instructions cause the processor to:
receive an initial image acquired by the camera when the subject support and/or the camera are in the first position relative to one another;
control at least one of the subject support and the camera to move from the first position to the second position relative to one another;
receive at least one intermediate image acquired by the camera when the subject support and/or the camera are in the at least one intermediate position relative to one another;
measure a displacement between the subject support and the camera along the linear path for the at least one intermediate image as at least one of the subject support and the camera are moved from the first position to the second position; and
calculate a height profile of the subject by comparing the initial image and the at least one intermediate image, wherein the height profile is at least partially calculated using the displacement between the subject support and the camera, wherein the height profile is descriptive of a spatially dependent height of the subject above the support surface.

2. The medical apparatus as claimed in claim 1, wherein the subject support is configured for:
moving relative to the camera from the first position to the second position along the linear path
positioning in the at least one intermediate position, and
measuring the displacement along the linear path between the first position and the at least one intermediate position.

3. The medical apparatus of claim 1, wherein the camera is a two-dimensional camera, wherein the height profile is calculated by detecting pixel displacements between combinations of the initial image and the at least one intermediate image.

4. The medical apparatus of claim 3, wherein the pixel displacements are used to calculate the height profile by:
dividing the initial image and the at least one intermediate image into multiple pixel regions;
identifying the pixel displacement of each of the multiple pixel regions; and
calculating the height profile by comparing the displacement of each of the multiple pixel regions to the displacement between the subject support and the camera.

5. The medical apparatus of claim 3, wherein detecting the pixel displacements between the combinations of the initial image and the at least one intermediate image is used to perform one or more of the following:
reduce signal to noise by averaging multiple height calculations;
reduce occluded regions using multiple height calculations of different combinations of the initial image and the at least one intermediate image; and
identify and reduce regions with no height calculation by comparing multiple height calculations.

6. The medical apparatus of claim 1, wherein the camera is a three dimensional camera, wherein the initial image is a first range image, wherein the at least one intermediate image is an intermediate range image, wherein the height profile is a combination of the initial image and the at least one intermediate image.

7. The medical apparatus of claim 6, wherein the initial image and the at least one intermediate image are combined at least partially by averaging.

8. The medical apparatus of claim 7, wherein the initial image and the at least one intermediate image are combined such that occluded regions from the height profile are removed.

9. The medical apparatus of claim 1, wherein the medical apparatus further comprises a medical imaging system for acquiring medical image data from an imaging volume, wherein the subject support is configured for moving into an imaging position, wherein at least a portion of the support surface is within the imaging volume when the subject support is in the imaging position.

10. The medical apparatus of claim 9, wherein execution of the instructions further causes the processor to:
fit a subject model to the height profile;
determine a region of interest using the subject model; and
control the subject support to move the region of interest within the imaging volume.

11. The medical apparatus of claim 10, wherein execution of the instructions further causes the processor to perform one or more of the following:
use the subject model to perform collision prediction with the medical imaging system, calculate a SAR estimate using the subject model,
calculate a subject weight using the subject model, and
calculate a subject height using the subject model.

12. The medical apparatus of claim 9, wherein the medical imaging system is any one of the following: a magnetic resonance imaging system, a position emission tomography system, a single photon emission tomography system, a computed tomography system, a combined positron emission tomography and magnetic resonance imaging system, a combined positron emission tomography and computed tomography system, a combined computer tomography and radiation therapy system, a combined computed tomography and positron emission tomography system, and a combined magnetic resonance imaging system and radiation therapy system.

13. The medical apparatus of claim 1, wherein the initial image and the at least one intermediate image are acquired as a video feed.

14. A non-transitory computer readable medium storing instructions for execution by a processor controlling a medical apparatus, wherein the medical apparatus comprises (i) a subject support for receiving a subject and (ii) a camera configured for imaging a support surface of the subject support, the subject support and the camera being movable relative to one another along a linear path between a first position, at least one intermediate position and a second position, the at least one intermediate position being located between the first position and the second position;
wherein execution of the instructions by the processor cause the processor to:
receive an initial image acquired by the camera when the subject support and the camera are in the first position relative to one another;
control at least one of the subject support and the camera to move from the first position to the second position relative to one another;
receiving at least one intermediate image acquired by the camera when the subject support and the camera are in the at least one intermediate position relative to one another;
measure a displacement between the subject support and the camera for the at least one intermediate image as at least one of the subject support and the camera are moved from the first position to the second position; and
calculate a height profile of the subject by comparing the initial image and the at least one intermediate image, wherein the height profile is at least partially calculated using the displacement between the subject support and the camera, wherein the height profile is descriptive of a spatially dependent height of the subject above the support surface.

15. A method of operating a medical apparatus, wherein the medical apparatus comprises (i) a subject support for receiving a subject and (ii) a camera configured for imaging a support surface of the subject support, the subject support and the camera being movable relative to one another along a linear path between a first position, at least one intermediate position and a second position, the at least one intermediate position being located between the first position and the second position; the method comprising:
acquiring an initial image with the camera when the subject support and the camera are in the at least one intermediate position relative to one another;
controlling the subject support to move at least one of the subject support and the camera from the first position to the second position relative to one another;
acquiring at least one intermediate image with the camera when the subject support and the camera are in the at least one intermediate position relative to one another;
measuring a displacement between the subject support and the camera for the at least one intermediate image as at least one of the subject support and the camera are moved from the first position to the second position; and
calculating a height profile of the subject by comparing the initial image and the at least one intermediate image, wherein the height profile is at least partially calculated using the displacement between the subject support and the camera, wherein the height profile is descriptive of a spatially dependent height of the subject above the support surface.

16. The method of claim 15, wherein and calculating the height profile comprises detecting pixel displacements between combinations of the initial image and the at least one intermediate image.

17. The method of claim 16, wherein calculating the height profile further comprises:
   dividing the initial image and the at least one intermediate image into multiple pixel regions;
   identifying the pixel displacement of each of the multiple pixel regions; and
   calculating the height profile by comparing the displacement of each of the multiple pixel regions to the displacement between the subject support and the camera.

18. The method of claim 16, further comprising:
   reducing signal to noise by averaging multiple height calculations using the detected pixel displacements;
   reducing occluded regions using multiple height calculations of different combinations of the initial image and the at least one intermediate image using the detected pixel displacements; and/or
   identifying and reducing regions with no height calculation by comparing multiple height calculations using the detected pixel displacements.

19. The method of claim 15, wherein the height profile is a combination of the initial image and the at least one intermediate image, and wherein the initial image and the at least one intermediate image are combined at least partially by averaging.

20. The method of claim 15, wherein the medical apparatus further comprises a medical imaging system for acquiring medical image data from an imaging volume, the method further comprising:
   fitting a subject model to the height profile;
   determining a region of interest using the subject model; and
   controlling the subject support to move the region of interest within the imaging volume.

* * * * *